United States Patent [19]

Mazurek

[11] Patent Number: 4,678,862

[45] Date of Patent: Jul. 7, 1987

[54] MOLTEN SALT HYDROCARBON CONVERSION PROCESS USING OXYGEN CONTAINING FEED

[75] Inventor: Harry Mazurek, Bala Cynwyd, Pa.

[73] Assignee: Atlantic Richfield Company, Los Angeles, Calif.

[21] Appl. No.: 825,029

[22] Filed: Jan. 31, 1986

[51] Int. Cl.4 .............................................. C07C 2/00
[52] U.S. Cl. ................................... 585/500; 585/415; 585/417; 585/541; 585/654; 585/656; 585/658; 585/661; 585/700; 585/943
[58] Field of Search .............. 585/500, 415, 417, 541, 585/654, 656, 658, 661, 700, 943

[56] References Cited

U.S. PATENT DOCUMENTS 3,081,256  3/1963  Hendal et al. ........................ 208/125
4,523,049  6/1985  Jones et al. ........................... 585/500

Primary Examiner—William R. Dixon, Jr.
Assistant Examiner—Cynthia A. Prezlock
Attorney, Agent, or Firm—Craig E. Larson

[57] ABSTRACT

Methane is converted into higher hydrocarbons by a process wherein a gas comprising methane and molecular oxygen is contacted at elevated temperatures with a molten salt mixture containing at least one reducible metal oxide.

6 Claims, No Drawings

MOLTEN SALT HYDROCARBON CONVERSION PROCESS USING OXYGEN CONTAINING FEED

BACKGROUND OF THE INVENTION

1. Field of the Invention

This invention relates to the synthesis of hydrocarbons from a methane source. A particular application of this invention is a method for converting natural gas to more readily transportable material using a molten salt methane conversion system which contains a reducible metal oxide and using a feed gas which contains molecular oxygen.

2. Description of the Pertinent Art

A major source of methane is natural gas. Other sources of methane have been considered for fuel supply (i.e., the methane present in coal deposits or formed during mining operations). Relatively small amounts of methane are also produced in various petroleum processes.

The composition of natural gas at the wellhead varies, but the major hydrocarbon present is methane. For example, the methane content of natural gas may vary within the range of about 40 to about 95 volume percent. Other constituents of natural gas include ethane, propane, butane, pentane (and heavier hydrocarbons), hydrogen sulfide, carbon dioxide, helium, and nitrogen.

Natural gas is classified as dry or wet, depending upon the amount of condensable hydrocarbons contained in it. Condensable hydrocarbons generally comprise $C_3+$ hydrocarbons, although some ethane may be included. Gas conditioning is required to alter the composition of wellhead gas; processing facilities usually being located in or near the production fields. Conventional processing of wellhead natural gas yields processed natural gas containing at least a major amount of methane.

Large-scale use of natural gas often requires a sophisticated and extensive pipeline system. Liquefaction has also been employed as a transportation means, but processes for liquefying, transporting and revaporizing natural gas are complex, energy intensive and require extensive safety precautions. Transport of natural gas has been a continuing problem in the exploitation of natural gas resources. It would be extremely valuable to be able to convert methane e.g., natural gas) to more readily transportable products. Moreover, direct conversion of olefins such as ethylene or propylene would be extremely valuable to the chemical industry.

It has been discovered that methane can be converted to higher hydrocarbons by contacting a methane-containing feed with a body of hot molten salt containing a reducible metal oxide. See commonly assigned co-pending U.S. patent application Ser. No. 747,548, filed June 21, 1985.

In procedures such as those described in said copending application, methane is converted to hydrocarbon products and coproduct water and the reducible metal oxide which is contained in the molten bath is depleted in active oxygen, resulting in a reduced metal oxide which is relatively inactive for the oxidative conversion of methane. It is taught that the reduced metal oxide can be regenerated by separate contact with an oxygen containing gas whereby the metal oxide in reduced form is reoxidized to active form. Such regenerations, however, require separate reaction zones or pulsed or phased reaction conditions which introduce added costs and inefficiencies to the processing sequence.

Mixed feed gases comprised of both methane and molecular oxygen have been used for the conversion of methane to higher hydrocarbons wherein the mixed gases are contacted with beds of contact solid comprised of a reducible metal oxide. See U.S. Pat. No. 4,523,049. The use of fluidized, fixed or moving beds of solids is taught. In such systems there are significant problems of heat transfer, attrition, and the like which have an adverse effect on practicality of the system.

SUMMARY OF THE INVENTION

The subject invention relates to an improved process for the conversion of methane to higher hydrocarbons. Specifically, in accordance with the invention a mixed feed containing both methane and molecular oxygen is contacted with a body of molten salt containing a reducible metal oxide, at elevated temperature whereby the methane reacts to form higher hydrocarbons while deactivation of the contact medium is avoided.

DETAILED DESCRIPTION OF THE INVENTION

In accordance with the present invention, a reaction feed gas containing both methane and molecular oxygen is passed into contact with a body of molten salt containing a reducible metal oxide at conditions of elevated temperature, whereby the methane reacts to form higher hydrocarbons and coproduct water while the contact agent is maintained in the active oxide form through reaction with molecular oxygen in the feed gas. In this way, the methane conversion activity of the system is maintained without the necessity for a separate step of reoxidizing a reduced form of the metal oxide contact agent.

In practice of the invention, a reaction feed gas comprised of both methane and molecular oxygen is provided. In addition to methane the hydrocarbon feedstock employed in the method of this invention may contain other hydrocarbon or non-hydrocarbon components. The methane content of the feedstock, however, will typically be within the range of about 40 to 100 vol. %, preferably within the range of about 80 to 100 vol. %, more preferably within the range of about 90 to 100 vol. %.

The oxygen-containing gas generally comprises molecular oxygen: other gases such as nitrogen and carbon oxides may be present. A preferred oxygen-containing gas is air.

The ratio of hydrocarbon feedstock to oxygen-containing gas is not narrowly critical to the present invention. Generally, it is desirable to control the hydrocarbon/oxygen molar ratio to avoid the formation of gaseous mixtures within the flammable region. It is preferred to maintain the volume ratio of hydrocarbon/oxygen within the range of about 0.1-100:1, more preferably within the range of about 1-50:1. Methane/air feed mixtures containing about 50 to 90 volume % methane have been found to comprise a desirable feedstream. Further dilution of the feedstream with gases such as nitrogen is not necessary.

The methane and molecular oxygen feed gas mixture is passed into contact with a body of molten salt which is maintained at elevated temperature above the melting point of the molten salt which is effective for accomplishing the desired methane reaction. Generally speaking, temperatures in the range of 500 to 1200° C. are suitable.

The molten salt contains a contact agent which is a composition comprising at least one reducible oxide of at least one metal. The reducible oxide produces higher hydrocarbon products, water and a reduced metal oxide when contacted with methane at a temperature selected within the range of about 500° to about 1000° C. The term "reducible" is used to identify those oxides of metals which are reduced by contacting methane at synthesizing conditions. The term "oxide(s) of metal(s)" includes: (1) one or more metal oxides (i.e., compounds described by the general formula $M_xO_y$, wherein M is a metal, 0 is oxygen, and the subscripts x and y designate the relative atomic proportions of metal and oxide in the composition); and/or (2) one or more oxygen-containing metal compounds; provided that such oxides and compounds have the capability of performing to produce higher hydrocarbon products as set forth herein.

Effective agents for the conversion of methane to higher hydrocarbons have previously been found to comprise reducible oxides of metals selected from a group consisting of manganese, tin, indium, germanium, antimony, lead, bismuth, and mixtures thereof. Reducible oxides of cerium, praseodymium, terbium, iron and ruthenium have also been found to be effective for the conversion of methane to higher hydrocarbons, particularly when the reducible metal oxide is associated with an alkali or alkaline earth metal compound. Particularly preferred contact agents comprise reducible oxides of manganese and mixtures of reducible oxides of manganese with other reducible metal oxides.

One class of preferred compositions is characterized by the substantial absence of catalytically effective amounts of nickel and the noble metals (e.g., rhodium, palladium, silver, osmium, iridium, platinum and gold) and compounds thereof to minimize the deleterious catalytic effects of such metals and compounds thereof. For example, at the conditions (e.g., temperature) under which the present composition are used, these metals tend to promote coke formation and oxides of these metals tend to promote the formation of combustion products ($CO_x$), rather than the desired hydrocarbons. The term "catalytically effective" is used to identify that quantity of nickel, the noble metals, and compounds thereof which, when present, substantially changes the distribution of products obtained when employing the compositions of this invention.

The reducible metal oxides may be associated with support materials such as silica, alumina, titania, magnesia, zirconia and the like and combinations thereof.

The contact agent particles should be finely divided to facilitate suspension in the molten salt mixture or should be molten or soluble in the molten salt mixture. When not molten or soluble in the molten salt medium, the contact agent is desirably uniformly suspended in the medium.

The molten salt should have a melting point below the lowest operating temperature in the system. Mixtures of salts may be usefully employed. In the case of binary or multiple mixtures the proportions of the molten salt components are preferably chosen as to correspond to a eutectic point. Salt compositions suitable for use in the method of this invention include (but are not broadly limited to) halides, phosphates, borates, nitrates, carbonates, sulfates, tungsten oxides, silicates, and molybdenum oxides of alkali metals, alkaline earth metals and mixtures thereof. Preferred salts are included in Table A.

TABLE A

| Salt | M.P. (°C.) | Mole % |
|---|---|---|
| $CaF_2$ | 682 | 100 |
| $BiF_3$ | 727 | 100 |
| $Na_2CO_3$ | 854 | 100 |
| $Li_2CO_3$ | 735 | 100 |
| $K_2CO_3$ | 891 | 100 |
| $Bi_2(MoO_4)_3$ | 643 | 100 |
| $Li_2WO_4$ | 742 | 100 |
| $Na_2WO_4$ | 696 | 100 |
| $Na_2Si_2O_5$ | 874 | 100 |
| $Li_2B_2O_4$ | 760 | 100 |
| $Li_2B_6O_{10}$ | 750 | 100 |
| $Li_2B_8O_{13}$ | 730 | 100 |
| $Li_2B_{10}O_{16}$ | 680 | 100 |
| $Na_2B_4O_7$ | 742 | 100 |
| $Na_2B_8O_{13}$ | 816 | 100 |
| $Na_2B_2O_5$ | 625 | 100 |
| $Li_2BO_2$ | 845 | 100 |
| $Na_2SO_4$ | 889 | 100 |
| $Li_2WO_4/Na_2WO_4$ | 490 | 45/55 |
| $Na_2CO_3/K_2CO_3$ | 710 | 56/44 |
| $Li_2SO_4$ | 859 | 100 |
| $Li_2CO_3/Na_2CO_3/K_2CO_3$ | 397 | 43.5/31.5/25.0 |
| KCl | 772 | 100 |
| LiCl | 610 | 100 |
| NaCl | 808 | 100 |
| $MgCl_2$ | 714 | 100 |

Of these, particularly suitable salts include lithium phosphate, sodium borate, lithium borate, and a mixture of lithium carbonate, sodium carbonate, and potassium carbonate eutectic at the selected operating temperatures.

In a preferred embodiment, the molten salt may be stabilized by the addition of additives. Suitable additives include sulfur dioxide and trioxide for sulfate systems, and carbon dioxide for carbonate systems.

In the molten salt mixture, it may be desirable to add inert particles as gas dispersers. The reaction zone may also be fitted with mechanical means to disperse the feed gas.

In the molten salt mixture, it is preferred that the contact agent comprise from about 1 to about 75 volume percent of the mixture, more preferably from about 10 to about 50 volume percent. In the homogeneous salt mixture, the weight percent of contact agent should range from about 1 to about 75 percent, more preferably from about 20 to about 60 weight percent.

Operating temperatures for contacting the methane with the contact agent are preferably selected within the range of about 500° to about 1000° C.; the particular temperature selected depending upon the particular reducible metal oxide(s) employed in the contact agent. For example, reducible oxides of certain metals may require operating temperatures below the upper part of the recited range to minimize sublimation or volatilization of the metals (or compounds thereof) during the methane contact. Examples include reducible oxides of indium, germanium and bismuth (operating temperatures will preferably not exceed about 850° C.).

Operating pressures for the methane contacting step are not critical to the presently claimed invention. However, both general system pressure and partial pressure of methane have been found to affect overall results. Preferred operating pressures are within the range of about 0.1 to about 30 atmospheres. The partial pressure of methane in the reaction zone is preferably maintained within the range of about 1 atmosphere to about 2 atmospheres.

The space velocity of the gaseous reaction streams are similarly not critical to the presently claimed invention, but have been found to affect overall results. Preferred total gas hourly space velocities are within the range of about 10 to 10,00 hr.$^{-1}$, more preferably within the range of about 600 to 40,000 hr.$^{-1}$.

The effluent from the contact zone contains higher hydrocarbon products (e.g., ethylene, ethane and other light hydrocarbons), carbon oxides, water, unreacted hydrocarbon (e.g., methane) and oxygen, and other gases present in the oxygen-containing gas fed to the contact zone. Higher hydrocarbons may be recovered from the effluent and, if desired, subjected to further processing using techniques known to those skilled in the art. Unreacted methane may be recovered and recycled to the contact zone.

The present invention is further illustrated by reference to the following Examples.

EXAMPLES

In the examples, the runs were made at about atmospheric pressure in a concentric alumina tube reactor (1-inch inside diameter, 14 inches in length). The gases were sparged via a ½-inch OD alumina tube, fitted with a ¼-inch OD alumina thermowell, into the closed alumina tube reactor. The gases bubbled through the molten salt mixture and travelled along the outside of the sparge tube and were collected overhead. The entire reactor was placed in a ½ inch ID tube furnace. The calculated L/D ratios were determined by a 1-inch tube diameter and the volume of the molten salt mixture in powdered form at room temperature. Conversions were low due to bubble size constraints and subsequent poor gas/catalyst contact. Larger L/D ratios and/or smaller bubble sizes would have increased the methane conversion. Small bubble sizes could have been achieved by sparging the gases through grates or by placing inerts such as alumina, silicon carbide, and silica particles dispersed in the molten salt mixture.

The reactor material of construction is not limited to alumina; however, the material should be prudently chosen to avoid adverse reaction with the potentially corrosive properties of some of the molten salt mixture. The reactor is brought up to temperature under a flow of heated nitrogen or argon and then switched to the methane and molecular oxygen mixture at the start of the run.

The experiment results presented include methane conversions and selectivity to higher hydrocarbons calculated on a molar basis. Results are based on gas chromatographic analysis of total reactor effluent.

EXAMPLE I

A powder mixture of 50% by weight NaMnO4 and 50% by weight of a eutectic carbonate mixture consisting on a molar basis of 43.5% $Li_2CO_3$, 31.5% $Na_2CO_3$ and 25.0% $K_2CO_3$ was placed in the reactor and heated to the reaction temperature. A feed gas mixture consisting by volume of 50% methane and 50% air was bubbled through the molten salt mixture at a rate of 200 mls/min. Results are shown in the following Table 1.

TABLE 1

| L/D | Temp. °C. | Flow Rate ml./min | Percent Conv. | Percent $C_2+$ |
|---|---|---|---|---|
| 7 | 860 | 200 | 5 | 94 |

EXAMPLE 2

The procedure of Example 1 was followed using a molten bath mixture of 50% by weight $MnSO_4$/50% by weight $Na_2SO_4$. The results are shown in the following Table 2.

TABLE 2

| L/D | Temp. °C. | Flow Rate ml./min | Percent Conv. | Percent $C_2+$ |
|---|---|---|---|---|
| 7 | 804 | 200 | 3.2 | 36 |
| 7 | 826 | 200 | 5.4 | 38 |
| 7 | 854 | 200 | 10.3 | 40 |
| 7 | 906 | 200 | 24.5 | 57 |

EXAMPLE 3

The procedure of Example 1 was followed using a molten bath mixture of 50% by weight $MnSO_4$ and 50% by weight $Li_2SO_4$, an L/D of 5 and a flow rate of 100 ml/min. The results are shown in the following Table 3.

TABLE 3

| L/D | Temp. °C. | Flow Rate ml./min | Percent Conv. | Percent $C_2+$ |
|---|---|---|---|---|
| 5 | 799 | 100 | 71.1 | 20 |
| 5 | 826 | 100 | 86.8 | 23 |
| 5 | 851 | 100 | 87.4 | 23 |

EXAMPLE 4

The procedure of Example 2 was followed except that the flow rate was increased to 400 ml/min. The results are shown in the following Table 4.

TABLE 4

| L/D | Temp. °C. | Flow Rate ml./min. | Percent Conv. | Percent $C_2+$ |
|---|---|---|---|---|
| 7 | 798 | 400 | 3.5 | 32 |
| 7 | 827 | 400 | 5.3 | 32 |
| 7 | 851 | 400 | 10.8 | 34 |
| 7 | 877 | 400 | 19.2 | 31 |
| 7 | 900 | 400 | 28.0 | 34 |

EXAMPLE 5

The general procedure of Example 1 was followed with different molten salt mixtures. Results are shown in the following Table 5.

TABLE 5

| Molten Salt Mixture Composition, wt. % | L/D | Temp. °C. | Flow Rate ml/min | Percent Conv. | Percent $C_2+$ |
|---|---|---|---|---|---|
| 50% NaMnO4/ | 5.5 | 809 | 200 | 16.3 | 24 |
| 50% $Li_2B_{10}O_{16}$ | 5.5 | 828 | 200 | 21.0 | 21 |
|  | 5.5 | 853 | 200 | 24.2 | 19 |
|  | 5.5 | 875 | 200 | 26.0 | 17 |
|  | 5.5 | 900 | 200 | 29.0 | 16 |
| 50% NaMnO4/ | 6 | 875 | 200 | 22.8 | 27 |
| 50% $Na_2Si_2O_5$ | 6 | 904 | 200 | 24.0 | 18 |
|  | 6 | 926 | 200 | 26.0 | 14 |
| 50% NaMnO4/ | 5.3 | 827 | 200 | 10.9 | 39 |
| 50% $Li_3PO_4$ | 5.3 | 850 | 200 | 12.4 | 41 |
|  | 5.3 | 874 | 200 | 20.2 | 33 |

TABLE 5-continued

| Molten Salt Mixture Composition, wt. % | L/D | Temp. °C. | Flow Rate ml/min | Percent Conv. | Percent C$_2$+ |
|---|---|---|---|---|---|
| 50% NaMnO$_4$/ | 6 | 851 | 200 | 25.5 | 21 |
| 50% Na$_2$B$_4$O$_7$ | 6 | 876 | 200 | 31.0 | 22 |
|  | 6 | 901 | 200 | 36.4 | 13 |

The general procedure of Example 1 was followed using a molten salt mixture of 20% by weight MnO and 80% by weight of a eutectic mixture comprised of 65 mol % LiPO$_3$ and 35 mol % KPO$_3$. Results are shown in the following Table 6.

TABLE 6

| L/D | Temp. °C. | Flow Rate l./hr. | Percent CH$_4$ Conv. | Percent O$_2$ Conv. | Percent C$_2$+ |
|---|---|---|---|---|---|
| 3.6 | 703 | 2 | 11 | 91 | 36 |
| 3.6 | 753 | 2 | 13 | 82 | 37 |
| 3.6 | 756 | 6 | 16 | 80 | 36 |
| 3.6 | 850 | 12 | 10 | 77 | 42 |
| 3.6 | 804 | 12 | 14 | 85 | 38 |

In all of the examples presented above there was no evidence of deactivation of the mixture of molten salt and reducible metal oxide thus demonstrating the effectiveness of molecular oxygen in the reaction feed mixture in maintaining the reducible metal oxide in the active form.

I claim:

1. A method useful for conversion of methane to higher hydrocarbons which comprises contacting a gas comprising methane and molecular oxygen with a molten salt mixture containing at least one reducible metal oxide at conditions to convert methane to said higher hydrocarbons while maintaining said reducible metal oxide in active form.

2. The method of claim 1 wherein said contacting is carried out at a temperature selected within the range of about 500° to about 1000° C.

3. The method of claim 1 wherein said gas comprises about 50 to about 90 volume % methane.

4. The method of claim 1 wherein the molten salt mixture comprises at least one reducible oxide of at least one metal selected from the group consisting of Mn, Sn, In, Ge, Sb, Pb, Bi, Ce, Pr, Tb, Fe, Ru and mixtures thereof.

5. The method of claim 1 wherein said molten salt mixture comprises at least one reducible oxide of Mn.

6. The method of claim 1 wherein the molten salt is selected from the group consisting of halides, phosphates, borates, nitrates, carbonates, sulfates, tungsten oxides, silicates and molybdenum oxides of alkali metals and alkali earth metals and mixtures thereof.

* * * * *